US012661226B2

(12) United States Patent
Abo-Auda

(10) Patent No.: US 12,661,226 B2
(45) Date of Patent: Jun. 23, 2026

(54) METHOD OF DELIVERING A TRANSCUTANEOUS DUAL VALVE REPLACEMENT DEVICE TO A PATIENT AND DEVICE THEREFOR

(71) Applicant: Cardio Voyage Innovations, LLC, McKinney, TX (US)

(72) Inventor: Wael Abo-Auda, Allen, TX (US)

(73) Assignee: Cardio Voyage Innovations, LLC, McKinney, TX (US)

( * ) Notice: Subject to any disclaimer, the term of this patent is extended or adjusted under 35 U.S.C. 154(b) by 668 days.

(21) Appl. No.: 18/041,622

(22) PCT Filed: Aug. 12, 2021

(86) PCT No.: PCT/US2021/045710
§ 371 (c)(1),
(2) Date: Feb. 14, 2023

(87) PCT Pub. No.: WO2022/036072
PCT Pub. Date: Feb. 17, 2022

(65) Prior Publication Data
US 2023/0320852 A1      Oct. 12, 2023

Related U.S. Application Data

(60) Provisional application No. 63/065,914, filed on Aug. 14, 2020.

(51) Int. Cl.
*A61F 2/24*          (2006.01)

(52) U.S. Cl.
CPC .......... *A61F 2/2436* (2013.01); *A61F 2/2418* (2013.01); *A61F 2210/0014* (2013.01);
(Continued)

(58) Field of Classification Search
CPC .................. A61F 2/2436; A61F 2/2418; A61F 2210/0014; A61F 2210/0057; A61F 2220/0008; A61F 2220/0091
See application file for complete search history.

(56) References Cited

U.S. PATENT DOCUMENTS

| 8,758,430 B2 | 6/2014 | Ferrari et al. |
| 9,066,800 B2 | 6/2015 | Clague et al. |
(Continued)

FOREIGN PATENT DOCUMENTS

| EP | 2695587 A1 | 2/2014 |
| EP | 2830536 B1 | 8/2017 |
(Continued)

*Primary Examiner* — Suzette J Gherbi
(74) *Attorney, Agent, or Firm* — The Webb Law Firm

(57) ABSTRACT

A method of delivering a transcutaneous dual valve replacement (TDVR) device to a patient includes the steps of advancing a guide catheter into the heart of the patient, advancing a support wire through the guide catheter and across the mitral valve of the heart of the patient, removing the guide catheter, advancing a delivery sheath over the support wire and across both the aortic valve and the mitral valve of the heart of the patient, advancing the TDVR device over the support wire and through the delivery sheath, removing the delivery sheath, expanding a first segment of the TDVR device in the mitral valve and a second segment of the TDVR device in the aortic valve, and removing the support wire.

18 Claims, 11 Drawing Sheets

(52) U.S. Cl.
CPC ................. *A61F 2210/0057* (2013.01); *A61F 2220/0008* (2013.01); *A61F 2220/0091* (2013.01)

(56) References Cited

U.S. PATENT DOCUMENTS

| | | | |
|---|---|---|---|
| 12,427,017 B2 * | 9/2025 | Al-Jilaihawi | ......... A61F 2/2418 |
| 2004/0206363 A1 * | 10/2004 | McCarthy | ............. A61F 2/2418 |
| | | | 623/2.18 |
| 2004/0210306 A1 * | 10/2004 | Quijano | ............... A61F 2/2475 |
| | | | 623/2.17 |
| 2005/0137686 A1 | 6/2005 | Salahieh et al. | |
| 2005/0251251 A1 | 11/2005 | Cribier | |
| 2007/0038293 A1 | 2/2007 | St.Goar et al. | |
| 2010/0217382 A1 | 8/2010 | Chau et al. | |
| 2010/0298927 A1 | 11/2010 | Greenberg | |
| 2011/0009956 A1 | 1/2011 | Cartledge et al. | |
| 2013/0231737 A1 | 9/2013 | McNamara et al. | |
| 2013/0261738 A1 * | 10/2013 | Clague | .................. A61F 2/2418 |
| | | | 623/2.11 |

FOREIGN PATENT DOCUMENTS

| | | | | |
|---|---|---|---|---|
| WO | WO-2009092782 A1 * | 7/2009 | ........... A61F 2/2418 |
| WO | 2010085659 A1 | 7/2010 | |

* cited by examiner

METHOD OF DELIVERING A TRANSCUTANEOUS DUAL VALVE REPLACEMENT DEVICE TO A PATIENT AND DEVICE THEREFOR

CROSS-REFERENCE TO RELATED APPLICATIONS

This application is the United States national phase of International Application No. PCT/US21/45710 filed Aug. 12, 2021, and claims priority to U.S. Provisional Application No. 63/065,914, filed Aug. 14, 2020, the disclosures of which are hereby incorporated by reference in their entireties.

BACKGROUND

Field of the Disclosure

The disclosed concept relates generally to a method of delivering a transcutaneous dual valve replacement (TDVR) device to a patient. The disclosed concept also relates to a TDVR device.

Description of the Related Art

Valve Heart disease is the third most common cause of cardiovascular disease in USA. Percutaneous replacement of heart valves is an incredible development in patient care and one of the great recent breakthroughs in cardiovascular medicine. However, it has been difficult to apply this technology to the mitral valve, due to proximity to the left ventricular outflow tract (LVOT). While transcatheter mitral valve replacement (TMVR) is an option for patients with mitral stenosis or regurgitation who are not suitable candidates for open surgical mitral repair or replacement, LVOT obstruction is a dreaded complication of TMVR, occurring in up to 40% of valve-in-MAC (mitral annular calcification), 5% of valve-in-ring, and 2% of valve-in-valve cases, and with 62% in-hospital mortality. Fear of LVOT obstruction is a leading cause for treatment exclusion, with 49% of screened patients for valve-in-MAC and 6% for valve-in-ring excluded in the MITRAL (Mitral Implantation of Transcatheter Valves) trial for predicted risk of LVOT obstruction.

TMVR-induced LVOT obstruction has two mechanisms. A fixed obstruction occurs when the anterior mitral valve leaflet is pushed toward the interventricular septum by the mitral valve prosthesis, creating a narrowed and elongated "neo-LVOT". A dynamic obstruction occurs when the narrowed neo-LVOT generates Bernoulli forces that draw the anterior mitral leaflet toward the interventricular septum during systole. A long anterior mitral leaflet may also prolapse back into the trans-catheter heart valve, interfering with valve closure and causing acute valve failure.

It is recommended that TMVR should probably be contraindicated in most of these patients who are at high risk of LVOT obstruction. Preventive strategies include either surgical transatrial leaflet resection, which involves cardiopulmonary bypass, associated morbidity, and reported 30-day mortality of 27%, or prophylactic alcohol septal ablation, which causes septal infarction, sacrifices myocardium and conduction tissue, may not be anatomically feasible or effective in all patients.

Therefore, a need exists for a well-designed percutaneous technology for mitral valve replacement that would improve the treatment of valvular heart disease. The disclosed concept addresses these challenges.

SUMMARY

In one aspect, a method of delivering a transcutaneous dual valve replacement (TDVR) device to a patient is provided. The method comprises advancing a guide catheter into the heart of the patient; advancing a support wire through the guide catheter and across the mitral valve of the heart of the patient; removing the guide catheter; advancing a delivery sheath over the support wire and across both the aortic valve and the mitral valve of the heart of the patient; advancing the TDVR device over the support wire and through the delivery sheath; removing the delivery sheath; expanding a first segment of the TDVR device in the mitral valve and a second segment of the TDVR device in the aortic valve; and removing the support wire.

In additional aspects, advancing the TDVR device includes pivoting the first segment with respect to the second segment in order to dispose the first segment in the mitral valve and the second segment in the aortic valve. In certain configurations, the first segment and the second segment are connected by a hinge, and when expanded in the mitral valve and the aortic valve, are disposed at an angle of less than 90° with respect to each other. In certain configurations, the method includes expanding the first segment of the TDVR device before the second segment. Optionally, the first segment and the second segment are each either self-expandable or balloon-expandable.

In additional aspects, advancing a guide catheter further includes introducing the guide catheter into the left ventricle of the heart of the patient, and rotating the guide catheter posteriorly to face the mitral valve. Another support wire may be advanced through a side port of a delivery catheter of the TDVR device and into the left ventricle of the heart of the patient. The side port may be positioned between the first segment and the second segment. Optionally, the method further includes advancing an anchor balloon into a pulmonary vein of the patient, and inflating the anchor balloon.

In additional aspects, the method further includes advancing a delivery sheath including employing a tapered flexible dilator to facilitate smooth delivery of the delivery sheath. The method may also include pulling the guide catheter before the guide catheter is removed in order to anchor the anterior mitral leaflet and push it close to the aortic-mitral continuity. The second segment maybe devoid of a collapsible prosthetic valve and functions to anchor the left ventricular outflow tract of the heart of the patient. The first segment and the second segment may be connected by a hinge, wherein the hinge includes a memory shape material. The hinge may also include a stretchable fabric connected to each of the first segment and the second segment.

In one aspect, a transcutaneous dual valve replacement (TDVR) device comprises a first segment comprising a first expandable outer stent tube configured to be deployed in an aortic valve of a heart of a patient; a second segment comprising a second expandable outer stent tube configured to be deployed in a mitral valve of the heart of the patient, the second segment being apart from the first segment; and a hinge connecting the first segment to the second segment, the first segment and the second segment being pivotable with respect to each other about the hinge.

In additional aspects, the first segment further includes a first collapsible prosthetic valve housed by the first expandable outer stent tube. The second segment further includes a second collapsible prosthetic valve housed by the second expandable outer stent tube. The first segment further includes a first collapsible prosthetic valve housed by the first expandable outer stent tube, with the second segment devoid of a collapsible prosthetic valve housed by the second expandable outer stent tube. Optionally, the hinge includes a memory shape material. The memory shape material may be Nitinol. The hinge may also include a stretchable fabric connected to each of the first segment and the second segment. The first segment and the second segment may each either self-expandable or balloon-expandable.

In still further aspects, the device may also include a miniaturized heart pump therein. The miniaturized heart pump may be provided in electrical communication with a support cable and an energy source, wherein the support cable may be configured for delivery through a transeptal approach. Optionally, the energy source may be a Subclavian Infraclavicular battery.

Further details and advantages of the various examples described in detail herein will become clear upon reviewing the following detailed description of the various examples in conjunction with the accompanying drawing figures.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

The following description is provided to enable those skilled in the art to make and use the described embodiments contemplated for carrying out the concept. Various modifications, equivalents, variations, and alternatives, however, will remain readily apparent to those skilled in the art. Any and all such modifications, variations, equivalents, and alternatives are intended to fall within the spirit and scope of the present concept.

In accordance with the disclosed concept, a Transcutaneous Dual Valve Replacement (TDVR) device 200, shown in FIGS. 6-9, using two connected segments, is provided. The configuration of the TDVR device 200 can be used to treat combined aortic and mitral valve pathology. In order to deploy the TDVR device 200 at aortic and mitral valve positions, an arterial access is attained using standard techniques, dilators and sheaths in the femoral artery location. The connecting hinge design allows for optimal exclusion of the anterior mitral leaflets, effectively eliminating the risk of LVOT obstruction complication. As will be discussed below, an alternative, truncated aortic segment configuration allows for the use of the device for mitral valve disease, while accomplishing effective LVOT obstruction mitigation. Additionally, methods for Trans-Aortic device delivery and deployment are provided.

Parts of the TDVR device 200 may be formed of any of several materials, such as flexible polymer materials, bioabsorbable materials, shape memory materials, or metals. While the shape of the TDVR device 200 has been depicted in illustrations, different shapes can be adopted while conforming to the general design principles of the disclosed concept.

These and other features will become readily apparent from the following description wherein embodiments of the disclosed concept are shown and described by way of illustration. As will be realized, the disclosed concept is capable of other and different embodiments and its several details may be capable of modifications in various respects, all without departing from the scope of the disclosed concept. Accordingly, the drawings and description are to be regarded as illustrative in nature and not in a restrictive or limiting sense.

Figure 11:
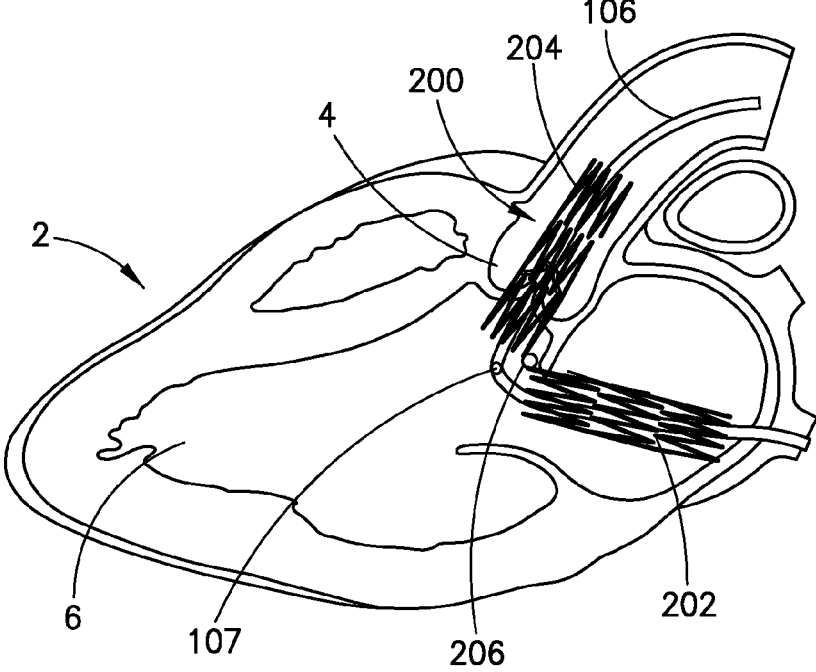
FIG. 11 is a schematic representation of the heart of FIG. 10 with the delivery sheath removed.

In accordance with the disclosed concept, a method of delivering the TDVR device 200 to a patient can be appreciated with reference to FIGS. 1-5, and 10-16. Once a standard access J-wire is advanced across the aortic valve of the patient, the method includes advancing a curved guide catheter 100 into the left ventricle 6 of the heart 2 of the patient (FIG. 1), advancing a support wire 102 through the guide catheter 100 and across the mitral valve 8 of the heart 2 of the patient (FIG. 2), and navigating the support wire 102 to one of the pulmonary veins. Next, the method includes removing the guide catheter 100 (e.g., preferably via a peal-away option) (FIG. 4), advancing a delivery sheath 104 over the support wire 102 and across both the aortic valve 4 and the mitral valve 8 of the heart 2 of the patient (FIG. 5), advancing the TDVR device 200 over the support wire 102 and through the delivery sheath 104 (FIG. 10), and removing the delivery sheath 104 (FIG. 11). When the delivery sheath 104 is removed, the TDVR device 200 is exposed and positioned in the aortic valve 4 and the mitral valve 8. Subsequently, by expanding a first segment 202 of the TDVR device 200 in the mitral valve 8 (FIG. 13) and a second segment 204 of the TDVR device 200 in the aortic valve 4 (FIG. 14), and removing the support wire 102 (FIG. 15) and catheters, the TDVR device 200 may be effectively delivered to the patient.

Figure 1:
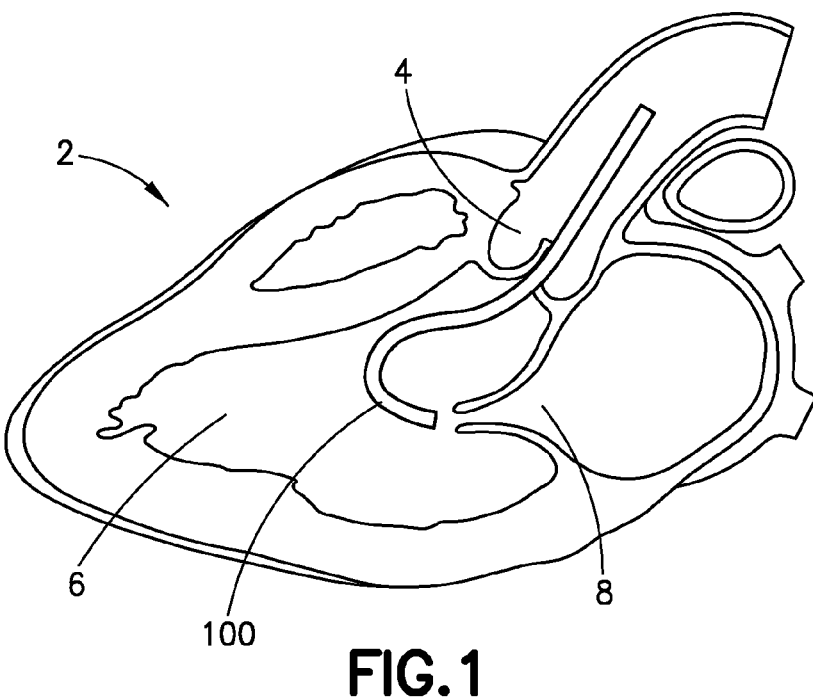
FIG. 1 is a schematic representation of a heart of a patient, with a guide catheter having been advanced into the left ventricle, in accordance with one non-limiting embodiment of the disclosed concept.
Figure 2:
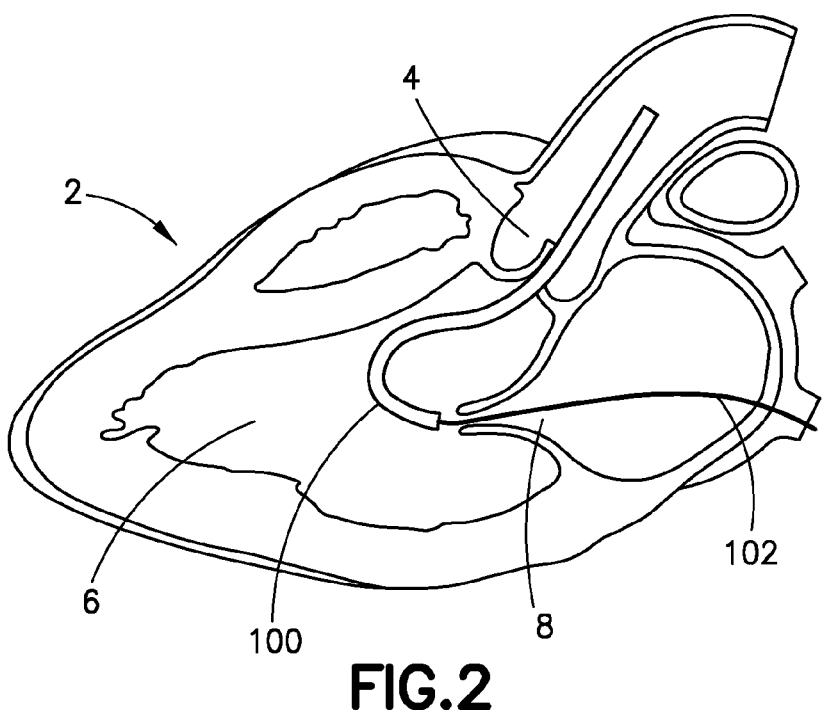
FIG. 2 is a schematic representation of the heart of FIG. 1, with a support wire having been advanced through the guide catheter and across the mitral valve.
Figure 3A:
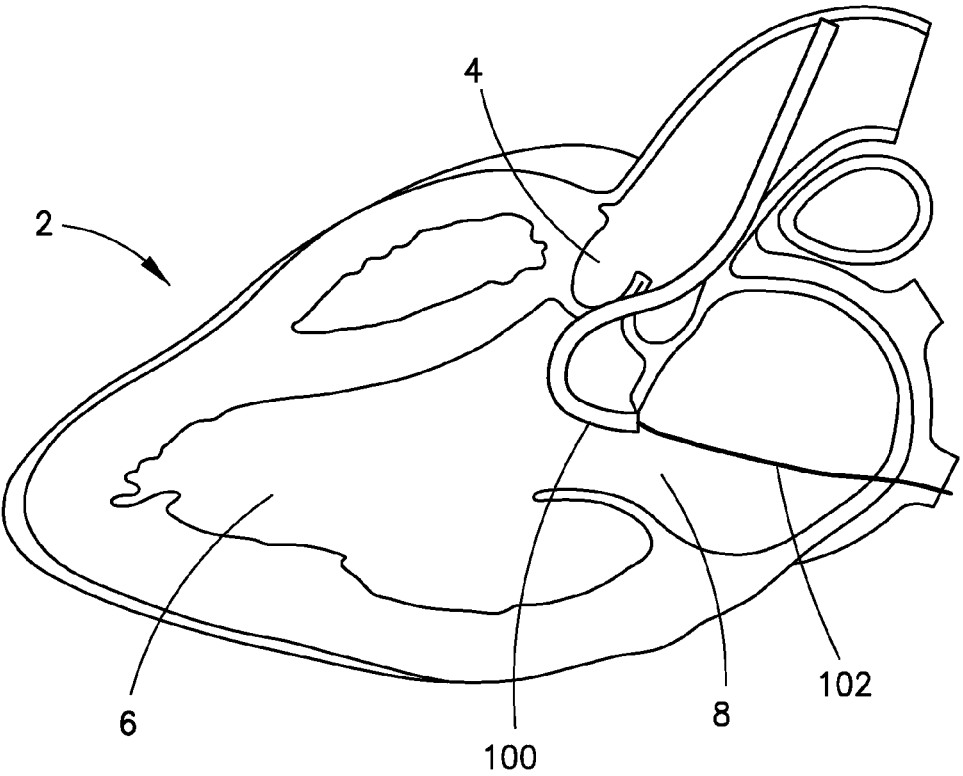
FIG. 3A is a schematic representation of the heart of FIG. 2 with the guide catheter in a retracted position.
Figure 3B:
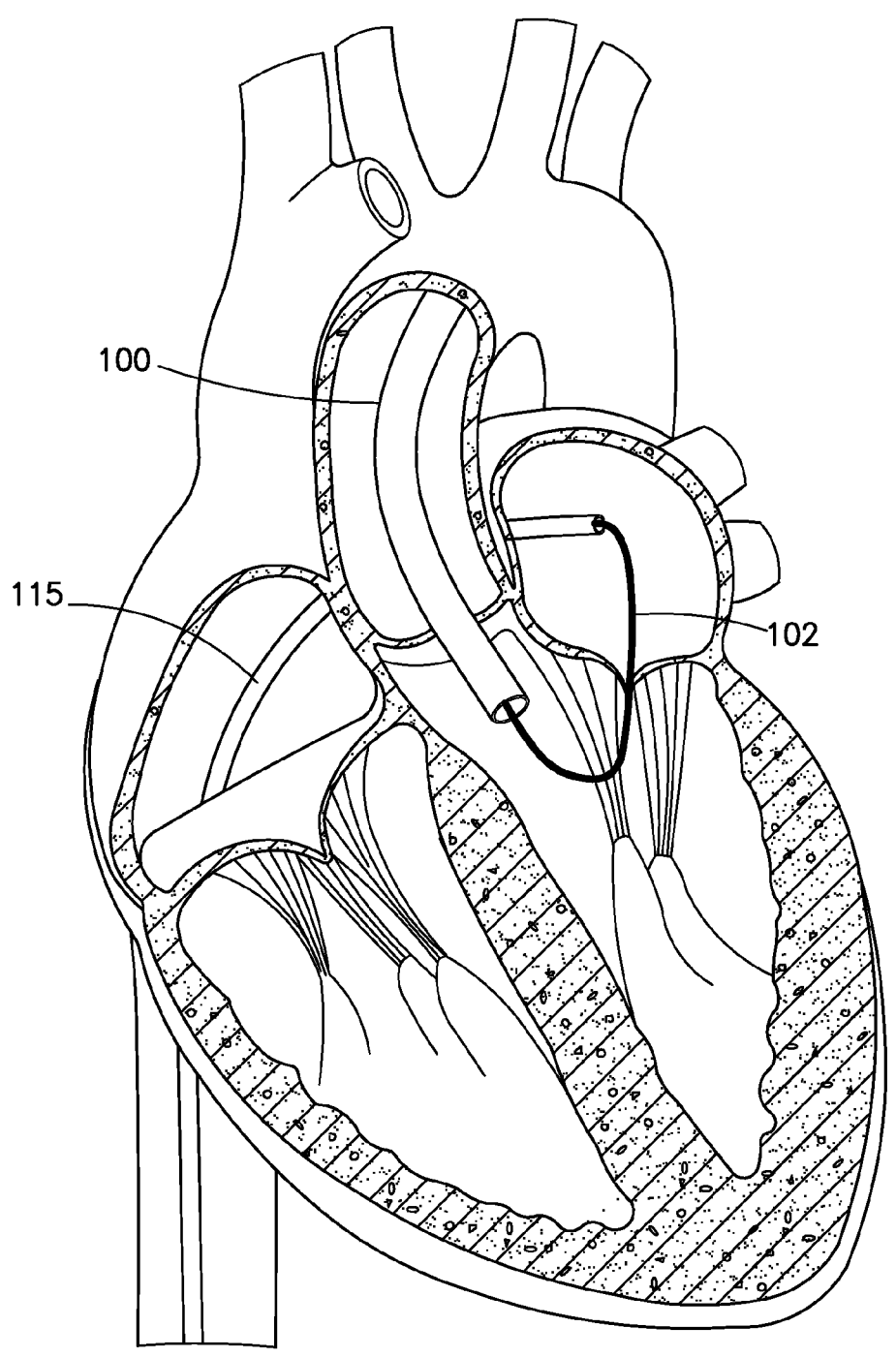
FIG. 3B is a schematic representation of a heart showing the support wire snared through a transeptal catheter and externally secured.
Figure 4:
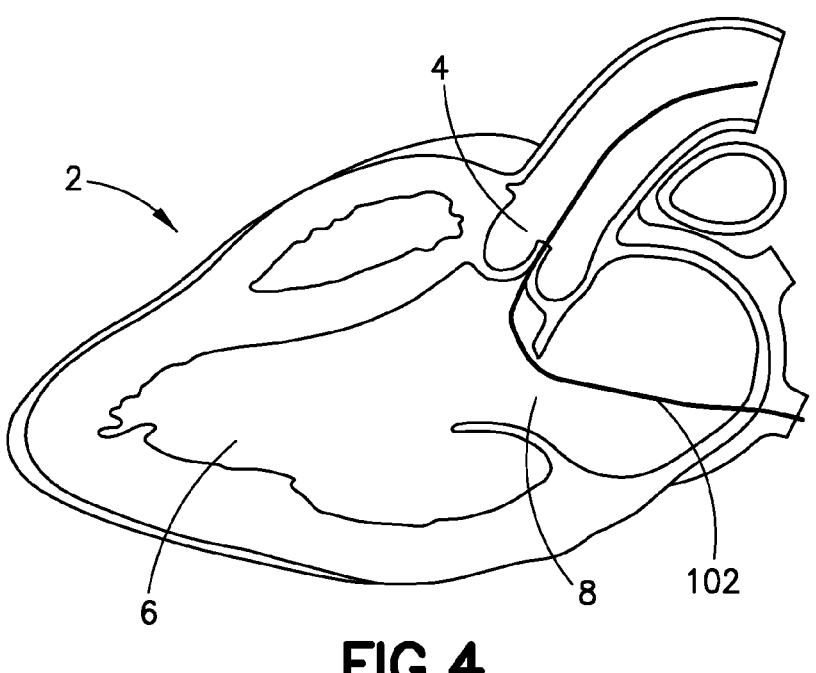
FIG. 4 is a schematic representation of the heart of FIG. 3A with the guide catheter having been removed.
Figure 5:
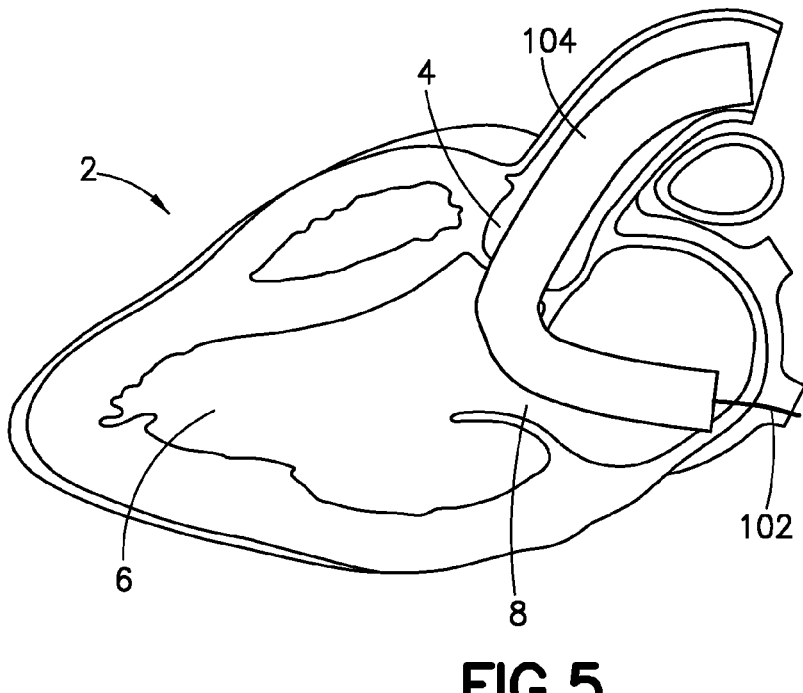
FIG. 5 is a schematic representation of the heart of FIG. 4 with a delivery sheath having been advanced over the support wire and across both the aortic valve and the mitral valve.
Figure 6A:
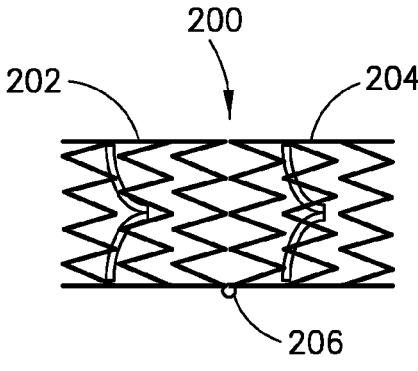
FIG. 6A is a schematic representation of a transcutaneous dual valve replacement (TDVR) device.
Figure 6B:
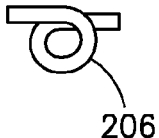
FIG. 6B is a schematic representation of a hinge for the TDVR device of FIG. 6A.
Figure 7:
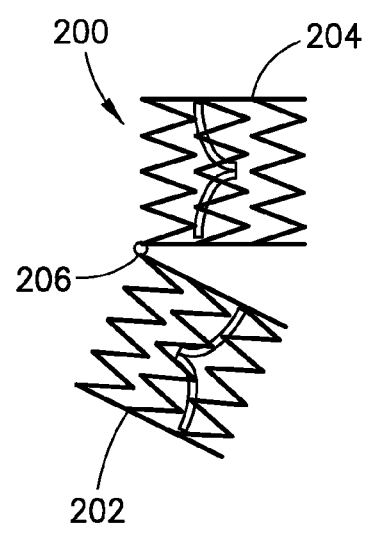
FIG. 7 is a schematic representation of the TDVR device of FIG. 6A with one segment pivoted about the hinge.
Figure 8:
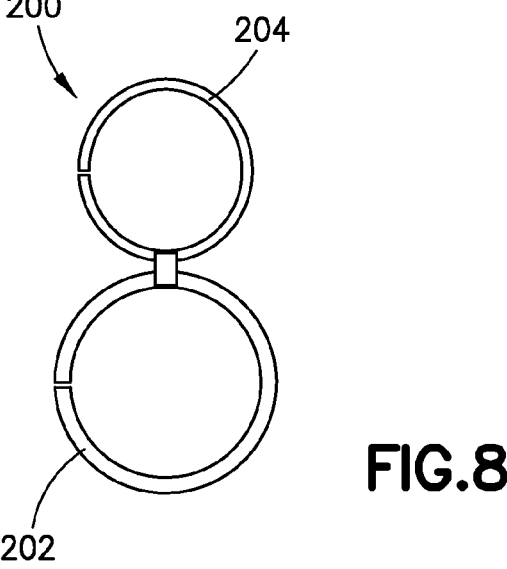
FIG. 8 is a schematic representation of a profile view of the TDVR device of FIG. 7.

Referring to FIG. 1, the method further includes introducing the guide catheter 100 into the left ventricle 6 of the heart 2 of the patient, and rotating the guide catheter 100 posteriorly to face the mitral valve 8. In this manner, and as shown in FIG. 2, when the support wire 102 is advanced, the support wire 102 can properly extend across the mitral valve 8. The method may also further include pulling the guide catheter 100 before the guide catheter 100 is removed in order to anchor the anterior mitral leaflet and push it close to the aortic-mitral continuity, as shown in FIG. 3A. Alternatively, as shown in FIG. 3B, the support wire 102 can be snared through a transeptal catheter 115, and secured externally, allowing for rigid support of further delivery steps.

Figure 12:
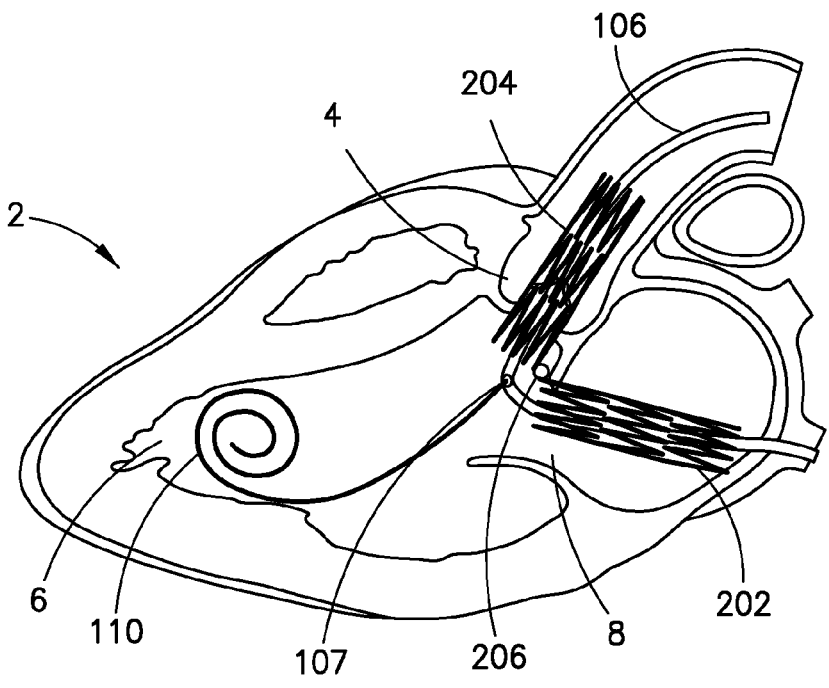
FIG. 12 is a schematic representation of the heart of FIG. 11 with another support wire advanced into the left ventricle.
Figure 13:
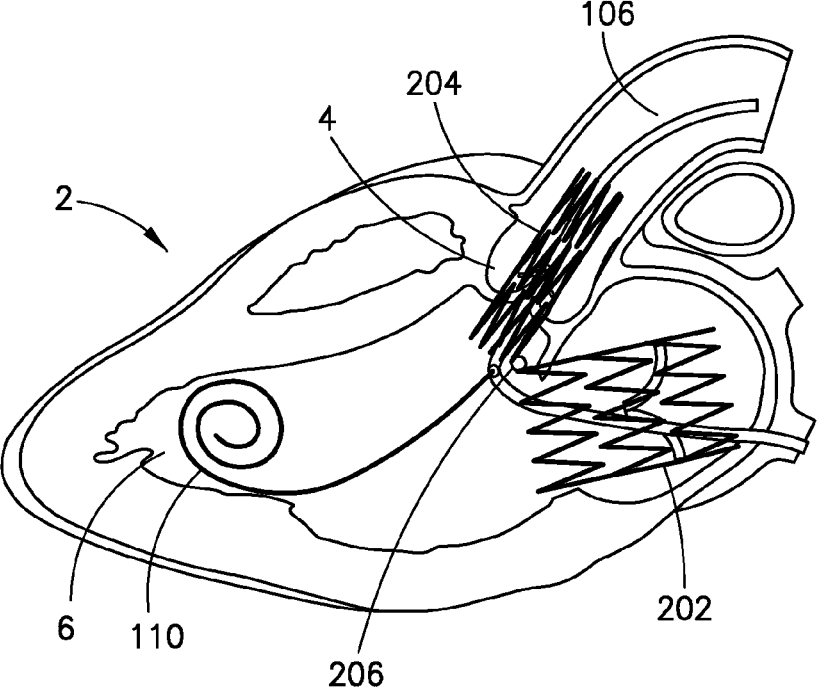
FIG. 13 is a schematic representation of the heart of FIG. 12 with a first segment of the TDVR device expanded in the mitral valve.
Figure 14:
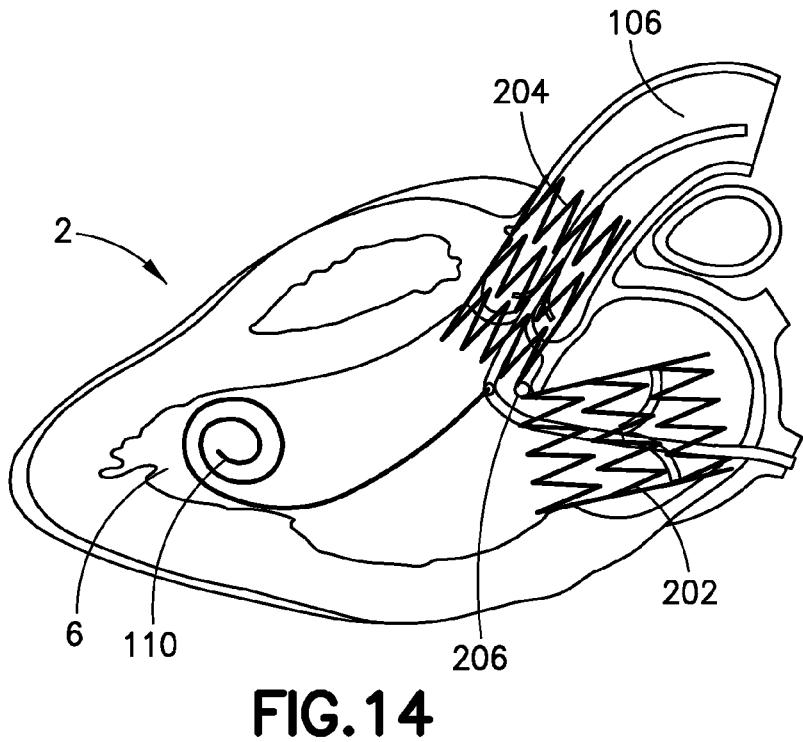
FIG. 14 is a schematic representation of the heart of FIG. 13 with a second segment of the TDVR device expanded in the aortic valve.

Referring to FIG. 12, the method may further include advancing another support wire 110 (e.g., without limitation, a safari wire) through a side port 107 of a delivery catheter 106 of the TDVR device 200 and into the left ventricle 6 of the heart 2 of the patient, in order to secure position of the TDVR device 200. As shown, the side port 107 is positioned between the first segment 202 and the second segment 204. An anchor balloon (not shown) may also be advanced into a pulmonary vein of the patient during the process, and then inflated, in order to secure position in the particular pulmonary vein during subsequent manipulations. Additionally, advancing the delivery sheath 104 may include employing a tapered flexible dilator (not shown) to facilitate smooth delivery of the delivery sheath 104. Optimal positioning can be accomplished using a variety of interventional operative techniques of push and pull maneuvers of the second support wire 110, anchor balloon, and the TDVR device 200. Once a satisfactory position is achieved, the method further includes expanding the first segment 202 (e.g., mitral valve segment) of the TDVR device 200 before the second segment 204 (e.g., aortic valve segment).

Because the mitral position is likely harder to secure, deploying the first segment 202 allows the second segment 204 to still have room to move a little for final positioning. This would not be the case if the second segment 204 were to be deployed first. That situation would commit the placement of the second segment 204, resulting in the first segment 202, the mitral segment, being more difficult to manipulate. Alternatively, an operator may choose to deploy the second segment 204 before the first segment 202, depending on optimal positioning needs.

Figure 15:
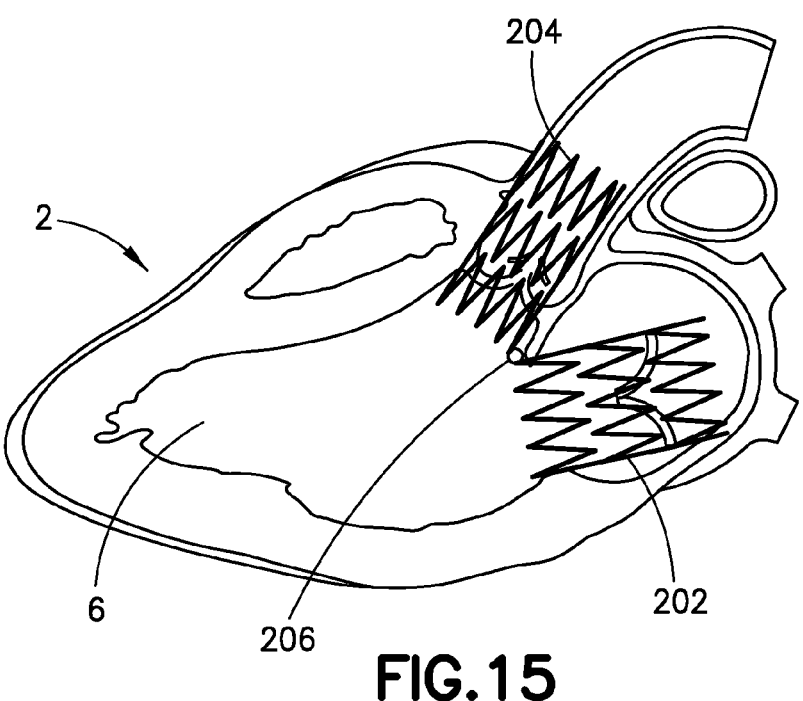
FIG. 15 is a schematic representation of the heart of FIG. 14 with the support wires and catheters removed.

Referring to FIGS. 6A-9, the TDVR device 200 will now be described. The TDVR device 200 includes the first segment 202 and the second segment 204 apart from the first segment 202. In one example embodiment, the first segment 202 and the second segment 204 are each either self-expandable or balloon-expandable. The first segment 202 includes a first expandable outer stent tube configured to be deployed in a mitral valve of a heart of a patient, and the second segment 204 includes a second expandable outer stent tube configured to be deployed in an aortic valve of the heart of the patient. The first segment 202 may further include a first collapsible prosthetic valve housed by the first expandable outer stent tube, and the second segment 204 may further include a second collapsible prosthetic valve housed by the second expandable outer stent tube. The outer stent tube and prosthetic valve can have a variety of configurations that can be adopted while conforming to the general design principles of the disclosed concept. A variety of size combinations of the two segments 202, 204 can be adopted to conform to the variable valve sizes in different patients. In this configuration, as shown in FIG. 15, the two segments 202, 204, connected by the hinge 206, are designed for combined aortic valve and mitral valve disease.

Figure 16:
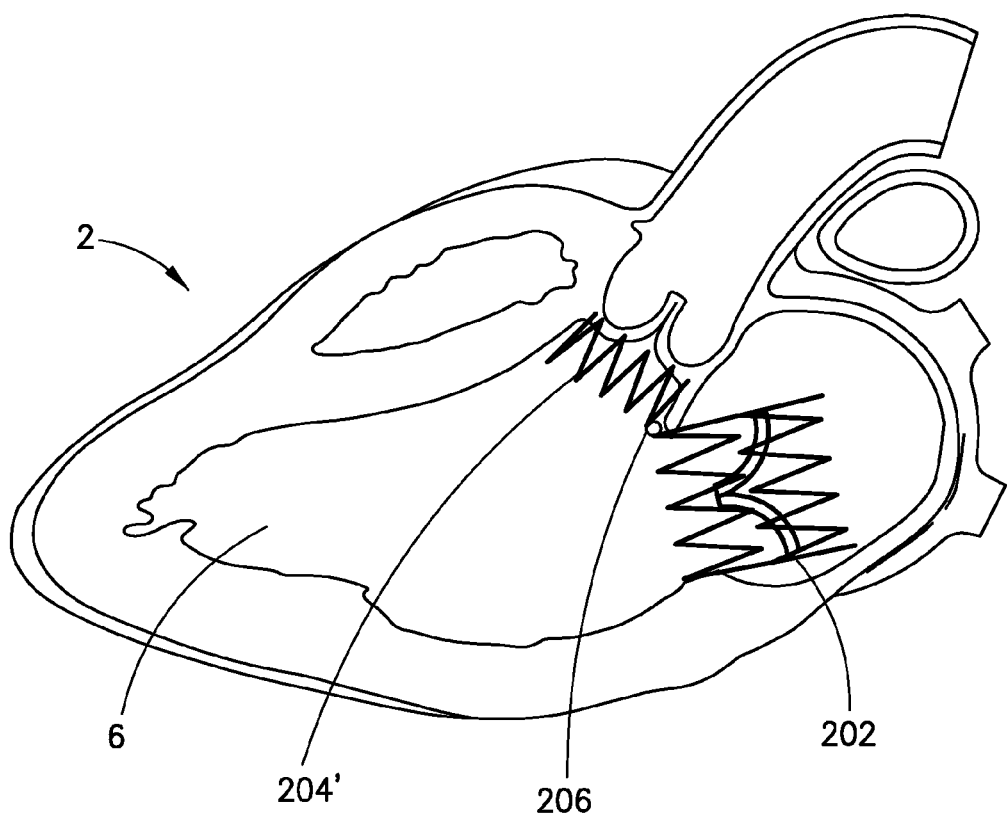
FIG. 16 is a schematic representation of the heart and TDVR device of FIG. 15, but with a truncated second segment.

Alternatively, the first segment 202 may further include a first collapsible prosthetic valve housed by the first expandable outer stent tube, and the second segment 204' may be devoid of a collapsible prosthetic valve housed by the second expandable outer stent tube. In this manner, as shown in FIG. 16, the second segment 204' functions to anchor the LVOT of the heart 2 of the patient. The second segment 204' in such a configuration is truncated, having no valve, and utilized as an LVOT anchor for optimal mitral valve placement, while avoiding LVOT obstruction pathology. This segment 204' excludes the anterior mitral apparatus. It will be appreciated that this configuration is advantageously targeted for isolated mitral valve pathology, e.g., for candidates without significant aortic valve pathology. Thus, this configuration is ideal for anterior mitral leaflet entrapment to prevent LVOT obstruction.

Figure 9:
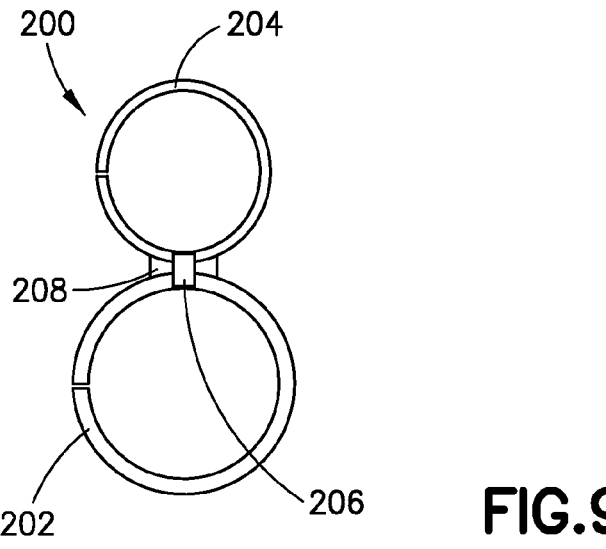
FIG. 9 is a schematic representation of another profile view of the TDVR device of FIG. 7, and shown with a flexible fabric material on either side of the hinge.
Figure 10:
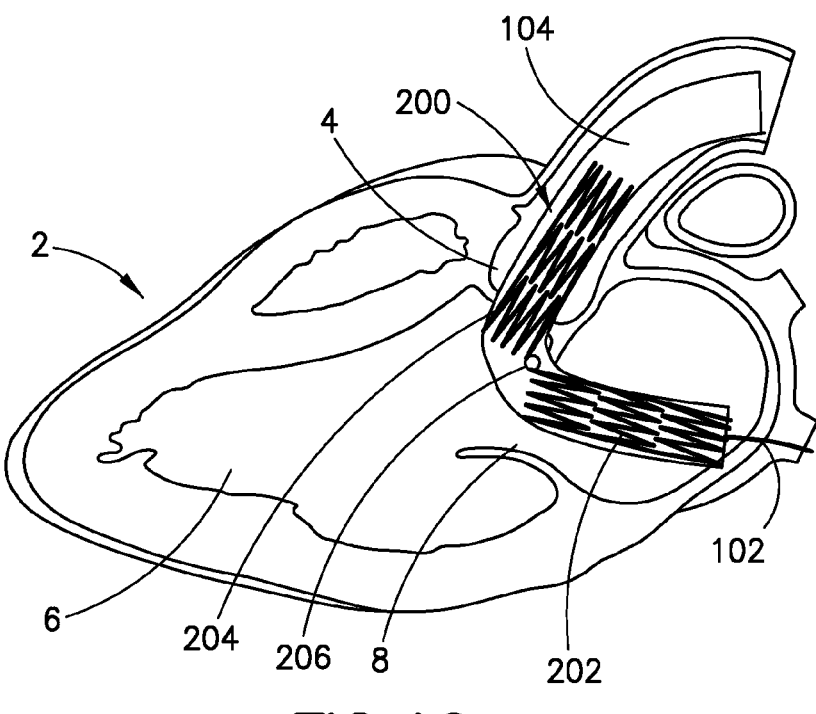
FIG. 10 is a schematic representation of the heart of FIG. 5 with the TDVR device advanced over the support wire and through the delivery sheath.

Moreover, as shown, the TDVR device 200 includes the hinge 206 connecting the first segment 202 to the second segment 204, with the first segment 202 and the second segment 204 being pivotable with respect to each other about the hinge 206. The hinge 206 is depicted with a spring like configuration, connecting the two valve segments 202, 204. Moreover, the hinge 206 may include a memory shape material, such as Nitinol. In one example embodiment, as shown in FIG. 9, the hinge 206 further includes a stretchable fabric 208 connected to each of the first segment 202 and the second segment 204. The purpose of this design is to trap and exclude the anterior mitral apparatus (Leaflets & chords), effectively eliminating the risk of LVOT obstruction complication. It is also contemplated herein, that hinge 206 and first segment 202 and/or second segment 204 may be made of the same material and/or material configuration. In one embodiment, the hinge 206 and the first segment 202 and/or second segment 204 may be made of the same mesh wire braiding to allow for a seamless transition therebetween. This may allow for optimized stretchability and conformability after and/or during deployment. As such, a variety of fabric designs, shapes and materials can be adopted while conforming to the general principles of the disclosed concept.

Advancing the TDVR device 200 over the support wire 102 includes pivoting the first segment 202 with respect to the second segment 204 in order to dispose the first segment 202 in the mitral valve 8 and the second segment 204 in the aortic valve 4. When the first segment 202 is expanded in the mitral valve 8 and the second segment is expanded in the aortic valve 4, the first and second segments 202, 204 are preferably disposed at an angle of less than 90° with respect to each other, as shown in FIGS. 7 and 14-16. This advantageously allows the first and second segments 202, 204 to conform to the general anatomic relation of the aortic valve 4 and mitral valve 8. It will be appreciated that the hinge 206 is set to an angle of less than 90°. When the hinge 206 is advanced in the delivery sheath 104, it is straightened, such that it is under tension and at an angle of about 180°. When the device is exposed, by retracting the delivery sheath 104, the hinge 206 will spring back to its memory angle of less than 90 degrees, to help achieve a proper anatomic relation of the first and second segments 202, 204.

In operation, the TDVR device 200 may be employed for the treatment of cardiac valves. Specifically, the disclosed concept provides an effective treatment of Mitral Valve Disease while addressing one or more limitations associated with currently developed devices. Mitral Valve Replacement is currently rather challenging, and often limited to a select subset of candidates. The TDVR device 200 provides a solution to these challenges associated with Mitral Valve Replacement. As a result, the TDVR device 200 and the associated method is ideal for poor surgical candidates with an otherwise short life expectancy.

The TDVR device 200 may also need to be capable of x-ray visualization by use of radiopaque fillers or marker bands, which may be fabricated from noble metals such as platinum or gold. These markers can be attached using a variety of common methods such as, for example, adhesive bonding, lamination between two layers of polymer, or vapor deposition. Visualization of the TDVR device 200 within the interior of the heart 2 during deployment may be provided by various means. For example, fluoroscopy can be utilized, and fluoro-visible (i.e., radio-opaque) dyes may be injected into the cardiac chambers so that the chambers of the heart and the related vasculature are visible using a fluoroscopy to achieve proper device placement when performing an implant procedure. Additionally, an ultrasonic probe may be positioned in the patient's esophagus (Transesophageal echocardiography (TEE)), on the surface of the patient's chest (Transthoracic echocardiography (TTE)), or in the heart (Intra-cardiac echocardiography (ICE)) to ultrasonically image the interior of the heart.

It is further contemplated herein, with reference to FIG. that the TDVR device 200 may be substantially or entirely enclosed in a fabric material, such as a covered stent graft 227, that allows for complete enclosure of the left atrial inflow and control of aortic outflow. In certain embodiments, the graft material can be modified to allow for partial exclusion of the left ventricular cavity, to allow for maintaining left ventricular viability.

Figure 17:
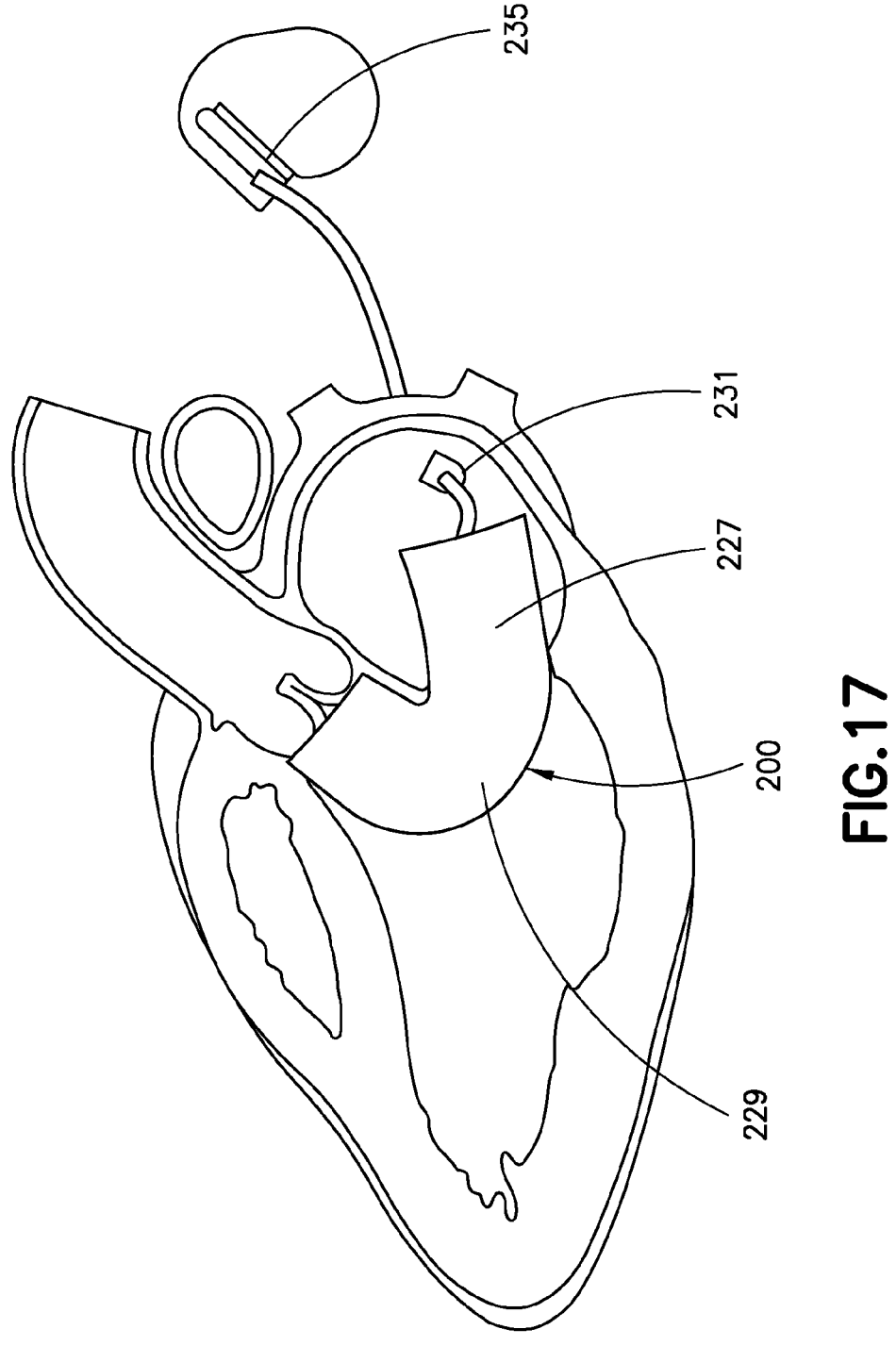
FIG. 17 is a schematic representation of a heart and TDVR device having a stent graft that houses a miniaturized heart pump therein.

It is also contemplated herein, as shown in FIG. 17, that the stent graft 227 may also house a miniaturized heart pump 229 therein. The support cable 231, including an energy source and control wires, may be externalized through a transeptal approach, passing though SVC, and the left subclavian vein, and may be connected to a Subclavian Infraclavicular battery 235. The battery may include a control unit, and may be charged and controlled wirelessly. This embodiment could operate as a minimally invasive total artificial heart support device, which can be utilized for patients with advanced heart failure, as a bridge device awaiting transplant.

Sheaths, dilators, catheters, and wire used herein can all be conventional marketed products or modifications thereof.

For example, sheaths can be formed from PTFE (e.g. Teflon) or polyamide (e.g. Nylon) material, polyethylene, polyurethane or vinyl, and other materials, or a combination of materials. Furthermore, radiopaque marker materials may be added to delivery sheath 104 so as to render it radiopaque.

Elements of one disclosed aspect can be combined with elements of one or more other disclosed aspects to form different combinations, all of which are considered to be within the scope of the present concept.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method of replacing a heart valve comprising:
providing a valve replacement device comprising:
a first segment comprising a first expandable outer stent tube configured to be deployed in a mitral valve of a heart of a patient;
a second segment comprising a second expandable outer stent tube configured to be deployed in a left ventricular outflow tract of the heart of the patient; and
a hinge connecting the first segment to the second segment, the first segment and the second segment being at least partially pivotable with respect to each other, wherein the hinge further comprises a stretchable fabric connected to each of the first segment and the second segment
wherein the first segment includes a first collapsible prosthetic valve housed within the first expandable outer stent tube, and the second segment does not include a collapsible prosthetic valve;
guiding the valve replacement device into the heart of the patient; and
deploying the valve replacement device such that the first expandable outer stent tube is positioned within the mitral valve of the heart of the patient, the second expandable outer stent tube is positioned within the left ventricular outflow tract of the heart of the patient in a position that does not interfere with the function of an aortic valve of the heart of the patient, and an anterior mitral valve leaflet of the heart of the patient is entrapped between the first expandable outer stent tube and the second expandable outer stent tube.

2. The method of claim 1, wherein, when the valve replacement device is deployed in the heart of the patient, the first segment and the second segment are disposed at an angle of less than 90° with respect to each other.

3. The method of claim 1, wherein deploying the valve replacement device comprises expanding the first segment of the valve replacement device in the mitral valve and expanding the second segment of the valve replacement device in the aortic valve.

4. The method of claim 1, wherein the first segment is deployed before the second segment.

5. The method of claim 1, wherein a length of the first segment in a direction of blood flow is greater than a length of the second segment in the direction of blood flow.

6. The method of claim 1, wherein the hinge comprises a memory shape material.

7. A method of replacing a heart valve comprising:
providing a valve replacement device comprising:

a first segment comprising a first expandable outer stent tube configured to be deployed in a mitral valve of a heart of a patient;

a second segment comprising a second expandable outer stent tube configured to be deployed in a left ventricular outflow tract of the heart of the patient; and a hinge connecting the first segment to the second segment, the first segment and the second segment being at least partially pivotable with respect to each other, wherein the first segment includes a first collapsible prosthetic valve housed within the first expandable outer stent tube, and the second segment does not include a collapsible prosthetic valve;

guiding the valve replacement device into the heart of the patient; and deploying the valve replacement device such that the first expandable outer stent tube is positioned within the mitral valve of the heart of the patient, the second expandable outer stent tube is positioned within the left ventricular outflow tract of the heart of the patient in a position that does not interfere with the function of an aortic valve of the heart of the patient, and an anterior mitral valve leaflet of the heart of the patient is entrapped between the first expandable outer stent tube and the second expandable outer stent tube, wherein the hinge further comprises a wing protrusion for the purpose of containing at least a portion of the anterior mitral leaflet to prevent LVOT obstruction.

8. The method of claim 1, wherein guiding the valve replacement device into the heart of the patient comprises:

advancing a guide catheter into the heart of the patient;

advancing a support wire through the guide catheter and across the mitral valve of the heart of the patient;

advancing a delivery sheath over the support wire and across both the aortic valve and the mitral valve of the heart of the patient;

advancing the valve replacement device over the support wire and through the delivery sheath; and removing the delivery sheath to deploy the valve replacement device.

9. The method of claim 8, further comprising removing the support wire and removing the guide catheter after deployment of the valve replacement device.

10. A method of replacing a heart valve comprising:

providing a valve replacement device comprising:

a first segment comprising a first expandable outer stent tube configured to be deployed in a mitral valve of a heart of a patient;

a second segment comprising a second expandable outer stent tube configured to be deployed in a left ventricular outflow tract of the heart of the patient; and a hinge connecting the first segment to the second segment, the first segment and the second segment being at least partially pivotable with respect to each other, wherein the first segment includes a first collapsible prosthetic valve housed within the first expandable outer stent tube, and the second segment does not include a collapsible prosthetic valve;

guiding the valve replacement device into the heart of the patient; and deploying the valve replacement device such that the first expandable outer stent tube is positioned within the mitral valve of the heart of the patient, the second expandable outer stent tube is positioned within the left ventricular outflow tract of the heart of the patient in a position that does not interfere with the function of an aortic valve of the heart of the patient, and an anterior mitral valve leaflet of the heart of the patient is entrapped between the first expandable outer stent tube and the second expandable outer stent tube, wherein guiding the valve replacement device into the heart of the patient comprises:

advancing a guide catheter into the heart of the patient;

advancing a support wire through the guide catheter and across the mitral valve of the heart of the patient;

advancing a delivery sheath over the support wire and across both the aortic valve and the mitral valve of the heart of the patient;

advancing the valve replacement device over the support wire and through the delivery sheath; and removing the delivery sheath to deploy the valve replacement device, wherein advancing the guide catheter into the heart of the patient further comprises introducing the guide catheter into the left ventricle of the heart of the patient, and rotating the guide catheter posteriorly to face the mitral valve.

11. The method of claim 8, wherein advancing the valve replacement device comprises pivoting the first segment with respect to the second segment in order to dispose the first segment in the mitral valve of the heart of the patient and the second segment in the aortic valve in the mitral valve of the heart of the patient.

12. A method of replacing a heart valve comprising:

providing a valve replacement device comprising:

a first segment comprising a first expandable outer stent tube configured to be deployed in a mitral valve of a heart of a patient;

a second segment comprising a second expandable outer stent tube configured to be deployed in a left ventricular outflow tract of the heart of the patient; and a hinge connecting the first segment to the second segment, the first segment and the second segment being at least partially pivotable with respect to each other, wherein the first segment includes a first collapsible prosthetic valve housed within the first expandable outer stent tube, and the second segment does not include a collapsible prosthetic valve;

guiding the valve replacement device into the heart of the patient; and deploying the valve replacement device such that the first expandable outer stent tube is positioned within the mitral valve of the heart of the patient, the second expandable outer stent tube is positioned within the left ventricular outflow tract of the heart of the patient in a position that does not interfere with the function of an aortic valve of the heart of the patient, and an anterior mitral valve leaflet of the heart of the patient is entrapped between the first expandable outer stent tube and the second expandable outer stent tube, wherein guiding the valve replacement device into the heart of the patient comprises:

advancing a guide catheter into the heart of the patient;

advancing a support wire through the guide catheter and across the mitral valve of the heart of the patient;

advancing a delivery sheath over the support wire and across both the aortic valve and the mitral valve of the heart of the patient;

advancing the valve replacement device over the support wire and through the delivery sheath; and removing the delivery sheath to deploy the valve replacement device, and advancing a second support wire through a side port of the guide catheter and into the left ventricle of the heart of the patient, wherein the side port is positioned between the first segment and the second segment.

13. The method of claim 8, further comprising:

advancing an anchor balloon into a pulmonary vein of the patient; and inflating the anchor balloon.

14. The method of claim 8, wherein advancing the delivery sheath further comprises employing a tapered flexible dilator to facilitate smooth delivery of the delivery sheath.

15. The method of claim 8, further comprising pulling the guide catheter before the guide catheter is removed in order to anchor the anterior mitral leaflet and push it close to the aortic-mitral continuity.

16. A valve replacement device comprising:

a first segment comprising a first expandable outer stent tube configured to be deployed in a mitral valve of a heart of a patient;

a second segment comprising a second expandable outer stent tube configured to be deployed in an aortic valve of the heart of the patient, the second segment being apart from the first segment; and a hinge connecting the first segment to the second segment, the first segment and the second segment being at least partially pivotable with respect to each other, wherein the hinge further comprises a stretchable fabric connected to each of the first segment and the second segment, an wherein the first segment includes a first collapsible prosthetic valve housed within the first expandable outer stent tube, and the second segment does not include a collapsible prosthetic valve.

17. The valve replacement device of claim 16, wherein a length of the first expandable outer stent tube is less than a length of the second first expandable outer stent tube.

18. The valve replacement device of claim 16, wherein the hinge comprises a memory shape material, and the hinge has a memory angle that disposes the first segment and the second segment at an angle of less than 90° with respect to each other.

* * * * *